United States Patent [19]

Dubreux et al.

[11] 4,159,991

[45] Jul. 3, 1979

[54] ACYLOXY-N,N'-DIACYLMALONAMIDES AND METHODS FOR THEIR PREPARATION

[75] Inventors: Bernard Dubreux, Francheville le Bas; Serve Y. Delavarenne, Francheville le Haut; Jean-Pierre Schirmann, Oullins, all of France

[73] Assignee: Produits Chimiques Ugine Kuhlmann, Paris, France

[21] Appl. No.: 826,478

[22] Filed: Aug. 22, 1977

[30] Foreign Application Priority Data

Sep. 1, 1976 [FR] France .................... 76 26324

[51] Int. Cl.² .............. C07C 143/90; C11D 1/28; C09F 5/00
[52] U.S. Cl. ............... 260/401; 260/404.5; 560/11; 560/43; 560/45; 560/47; 560/61; 560/74; 560/110; 560/111; 560/100; 560/107; 560/149; 560/156; 560/157; 560/179; 560/185; 560/187; 560/227; 560/229; 560/226; 560/251; 560/254; 560/255; 560/105; 560/228
[58] Field of Search ....... 260/400, 404.5 R, 404.5 CN, 260/401; 560/100, 110, 107, 251, 11, 43, 45, 47, 61, 74, 111, 149, 156, 157, 179, 185, 187, 227, 229, 226, 254, 255

[56] References Cited

U.S. PATENT DOCUMENTS 808,748  1/1906  Hofmann ..................... 560/110

OTHER PUBLICATIONS

Cossi et al., Chemical Abstracts, 135681d, vol. 78 (1973).
Ho Chemical Abstracts vol. 82:85423f (1975).

*Primary Examiner*—John Niebling
*Attorney, Agent, or Firm*—Brooks, Haidt, Haffner & Delahunty

[57] ABSTRACT

α-Acyloxy-N,N'-diacylmalonamides of the formula

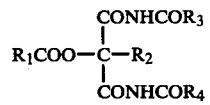

wherein $R_1$, $R_2$, $R_3$, and $R_4$ are the same or different and are hydrogen, straight chain or branched alkyl radicals having from one to eleven carbon atoms, or hydrocarbon radicals with six to twelve carbon atoms and comprising at least one aromatic ring, are novel compounds prepared by the action of a mixture of carboxylic acids $R_3COOH$ and $R_4COOH$ upon an α-acyloxymalononitrile, $R_1COO-C(CN)_2-R_2$, in the presence of an acid catalyst and are useful as intermediates in organic synthesis and low temperature activators in bleaching or scouring compositions.

12 Claims, No Drawings

ACYLOXY-N,N'-DIACYLMALONAMIDES AND METHODS FOR THEIR PREPARATION

BACKGROUND OF THE INVENTION

The present invention relates to novel polyfunctional compounds, and more particularly it relates to α-acyloxy-N-N'-diacylmalonamides and to their method of preparation by the action of a carboxylic acid or of a mixture of carboxylic acids upon an α-acyloxymalononitrile in the presence of an acid catalyst.

It is known that by the action of a carboxylic acid anhydride upon hydrocyanic acid or its salts, an α-acyloxymalononitrile, $R_1COO$—$C(CN)_2$—$R_2$ (II), is obtained in good yields. It is likewise known that at high temperatures and in the presence of a catalytic quantity of perchloric acid, the addition of a carboxylic acid to a nitrile can be performed in order to obtain N-acylated amides.

THE INVENTION

The α-acyloxy-N,N'-diacylmalonamides of the present invention conform to the formula:

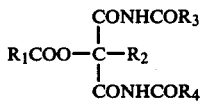

(I)

wherein $R_1$, $R_2$, $R_3$, and $R_4$, identical or different, are chosen among hydrogen, straight-chain or branched alkyl radicals with from one to eleven carbon atoms, or hydrocarbon radicals with from six to twelve carbon atoms and comprising at least one aromatic ring, optionally substituted by one or more groups such as nitro, hydroxy, alkoxy, carboxylic acid ester or amide, ether oxide, amino, sulfoxide, sulfone, or sulfonic acid groups; by a halogen; fluorine, chlorine, bromine, or iodine; or by a halogenated group and more particularly a halogenated methyl group. The preferred halogenated methyl groups are the mono-, di-, or trichloromethyl radicals and the mono-, di-, or trifluoromethyl radicals.

It has been surprisingly discovered, according to the present invention, that by treating an α-acyloxymalononitrile of the formula $R_1COO$—$C(CN)_2$—$R_2$ (II), wherein $R_1$ and $R_2$ have the meaning given hereinbefore, with a carboxylic acid RCOOH (R being $R_3$ or $R_4$) or with a mixture of carboxylic acids $R_3COOH$ and $R_4COOH$, wherein $R_3$ and $R_4$ have the meaning given hereinbefore, it is possible to perform, under mild conditions and in good yields, what corresponds exactly to the addition of an acid to each of the nitrile functions and thus to obtain α-acyloxy-N,N'-diacylmalonamides (I).

It has likewise been discovered according to this invention that the synthesis of the α-acyloxy-N,N'-diacylmalonamides can be performed directly from hydrocyanic acid or from cyanides by treating them first with a carboxylic acid anhydride, then in a second step with the carboxylic acid which is a by-product of the first reaction in the presence of various acid catalysts without isolating the intermediate α-acyloxymalononitrile (II). In this latter case $R_3$ and $R_4$ are the same and the same as $R_1$ or $R_2$.

The carboxylic acids which can be used in the present invention are preferably formic, acetic, propionic, butyric, isobutyric, valeric, caproic, heptanoic, caprylic, capric, lauric, stearic, benzoic, phenylacetic, toluic, naphthoic, and mono-, di- and trifluoro or -chloroacetic acids. The anhydrides which can be used in the present invention are preferably the simple or mixed anhydrides derived from the above acids.

The acid catalysts which can be used according to the invention are for example perchloric, hydrochloric, hydrobromic, phosphoric, polyphosphoric, paratoluene sulfonic, or sulfuric acids, aluminum chloride, zinc chloride, or boron trifluoride.

In order to carry out the method, it is possible either to bring derivative (II), the catalyst, and the acid, (the last playing the part of a solvent), into contact in any order; however, it is most frequently preferred to dissolve the catalyst in the acid previously and then to add compound (II) to this solution progressively, or, when starting with hydrocyanic acid or a cyanide, to treat the cyano material with a slight excess of anhydride in the presence of a catalytic quantity of triethylamine; thereafter, when the formation of the malononitrile is practically complete, to add the mixture to a solution of the acid catalyst in the carboxylic acid.

The addition of the carboxylic acid to the α-acyloxymalononitrile is performed at a temperature of between 0° and 100° C., preferably between 20° and 60° C. The optimum value, which can easily be determined by one skilled in the art after reading the present disclosure, may vary according to the particular reactivity of the reagents and of the catalyst used.

The addition of anhydride to hydrocyanic acid or to the cyanides followed by the action upon the intermediate product formed of the carboxylic acid which is a by-product, is performed under the same temperature conditions.

The reagents are advantageously used in stoichiometric proportions, although one or the other may be in deficit or in excess with respect to these proportions. The catalyst used is added at the rate of 0.01% to 10% by weight of the total reaction mixture.

The α-acyloxy-N,N'-diacylmalonamides obtained are solids which are isolated by filtration after concentration and which are purified by methods well known to one skilled in the art, for example, by recrystallization.

These novel polyfunctional compounds constitute intermediates in organic synthesis. They also find application in bleaching or scouring compositions, where they play the part of activators for the persalts, more particularly for sodium perborate and percarbonate.

The following examples are given to illustrate embodiments of the invention as it is presently preferred to practice it. It will be understood that these examples are illustrative, and the invention is not to be considered as restricted thereto except as indicated in the appended Claims.

EXAMPLE I

Into a 500 ml flask containing 16.8 ml of 70° Baumé sulfuric acid and 67.2 g of acetic acid, is charged during 90 minutes whilst agitating, a solution of 77.3 g of 1-acetoxy-1,1-dicyanoethane in 67.2 g of acetic acid. The temperature is maintained at 50° C. An abundant precipitate forms 15 minutes after the end of the introduction. Three hundred milliliters of water is then added to the mixture and the precipitate is filtered and then washed with 100 ml of water and dried.

One hundred and four grams of α-acetoxy-α-methyl-N,N'-diacetylmalonamide is recovered.

Melting point: 192° C., Yield: 72%.

The structure of the product is confirmed by elementary analysis and by the characteristics of the infra-red (IR) and nuclear magnetic resonance (NMR) spectra.

Analysis: Theory % C: 46.51; H 5.46; N: 10.85; Measured % C: 46.40; H 5.69; N: 10.88; C: 46.54; H 5.72; N: 10.95

IR: $\nu\text{cm}^{-1}$ = 3270, 3180, 2990, 1740, 1705, 1500, 1370, 1220, 720.

NMR (DMSO $d_6$) δ (ppm) ref HMDS: 1.7 (3H), 2.2 (3H), 2.3 (6H), 10.5 (2H).

EXAMPLE II

Into a 500 ml flask containing 225 g of acetic anhydride and 6.6 ml of triethylamine, is charged during one hour and with agitation, 54 g of hydrocyanic acid. The temperature is maintained between 30° and 35° C. When the addition is complete, 12 ml of triethylamine is added, and then the mixture is heated to 50° C. for 5 hours.

After cooling, 100 g of this mixture is poured in 30 minutes into a second flask maintained at 50° C. and containing 30 g of acetic acid and 7.5 ml of 70° Baumé sulfuric acid. A precipitate is formed which after cooling is treated with 200 ml of water, filtered, washed with 100 ml of water, and dried. In this way 73.5 g of α-acetoxy-α-methyl-N,N'-diacetylmalonamide is isolated, which corresponds to a yield of 84% referred to the hydrocyanic acid used.

EXAMPLE III

The procedure of Example II is followed, but the acetic anhydride is replaced by propionic anhydride. Starting with 31 g of propionic anhydride, 2.1 ml of triethylamine, 5.8 g of hydrocyanic acid, 3 ml of 70° Baumé sulfuric acid and 10 g of propionic acid, 7.5 g of α-propionyloxy-α-ethyl-N,N'-dipropionylmalonamide (melting point 90° C.) is obtained, which corresponds to a yield of 21%, referred to the hydrocyanic acid used.

IR: $\nu\text{cm}^{-1}$: 3260, 2980, 2940, 1755, 1710, 1690, 1470, 1360, 1180, 1080, 840, 800.

NMR (DMSO d6): δ (ppm) ref HMDS: ≈1 (12H) m, 2.2 (2H) quadruplet, 2.6 (6H) m, 10.5 (2H).

EXAMPLE IV

Following the operative procedure of Example I, but replacing the acetic acid by propionic acid, α-acetoxy-α-methyl-N,N'-dipropionylmalonamide is obtained in a 69 percent yield.

Melting point: 190° C.

IR: $\nu\text{cm}^{-1}$ 3260, 3180, 2980, 2940, 1750, 1490, 1370, 1230, 1160, 870, 720.

NMR (DMSO d6) δ (ppm) ref HMDS: 0.97 (6H) triplet, 1.69 (3H), 2.17 (3H), 2.60 (4H) quadruplet, 10.4 (2H).

What is claimed is:

1. α-Acyloxy-N,N'-diacylmalonamides of the formula

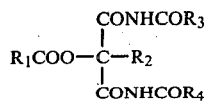

wherein $R_1$, $R_2$, $R_3$, and $R_4$ are the same or different and are hydrogen, straight-chain or branched-chain alkyl radicals having from one to eleven carbon atoms, or hydrocarbon radicals having from six to twelve carbon atoms and containing at least one aromatic ring.

2. α-Acyloxy-N,N'-diacylmalonamides according to claim 1 wherein at least one radical is substituted by a nitro, hydroxy, alkoxy, carboxylic ester or amide, ether oxide, amino, sulfoxide, sulfone, or sulfonic acid group; by fluorine, chlorine, bromine, or iodine; or by a halogenated hydrocarbon group.

3. α-Acyloxy-N,N'-diacylmalonamides according to claim 2 wherein the halogenated hydrocarbon group is a halogenated methyl radical.

4. α-Acyloxy-N,N'-diacylmalonamides according to claim 3 wherein the halogen is chloro or fluoro.

5. α-Acyloxy-N,N'-diacylmalonamides according to claim 4 wherein the halogenated methyl radical is trifluoromethyl or trichloromethyl.

6. A process for preparation of the acyloxydiacylmalonamides of claim 1 which comprises reacting an α-acyloxymalononitrile having the formula $R_1COO-C(CN)_2-R_2$ with at least one carboxylic acid having the formula $R_3COOH$ or $R_4COOH$ in the presence of an acid catalyst.

7. A process according to claim 6 wherein the α-acyloxymalononitrile is produced in situ by the reaction of hydrogen cyanide or a metal cyanide with a carboxylic acid anhydride to form the nitrile and carboxylic acid and wherein the carboxylic acid is reacted with the nitrile upon addition of the acid catalyst.

8. A process according to claim 7 wherein the anhydride is a simple or mixed anhydride of formic, acetic, propionic, butyric, isobutyric, valeric, caproic, heptanoic, caprylic, capric, lauric, stearic, benzoic, phenylacetic, toluic, naphthoic, mono-, di- or trifluoro, or -chloroacetic acids.

9. A process according to claim 6 wherein the carboxylic acid is formic, acetic, propionic, butyric, isobutyric, valeric, caproic, heptanoic, caprylic, capric, lauric, stearic, benzoic, phenylacetic, toluic, naphthoic, mono-, di- or trifluoro, or -chloroacetic acid or a mixture of two or more thereof.

10. A process according to claim 6 wherein the acid catalyst is perchloric, hydrochloric, hydrobromic, phosphoric, polyphosphoric, paratoluene sulfonic, or sulfuric acid, or aluminum chloride, zinc chloride, or boron trifluoride.

11. A process according to claim 6 wherein the catalyst used is added at the rate of 0.01 to 10% by weight of the total reaction mixture.

12. A process according to claim 6 wherein the reaction is performed at a temperature between 0° and 100° C.

* * * * *